United States Patent

Uflacker

[11] Patent Number: 5,713,948
[45] Date of Patent: Feb. 3, 1998

[54] ADJUSTABLE AND RETRIEVABLE GRAFT AND GRAFT DELIVERY SYSTEM FOR STENT-GRAFT SYSTEM

[76] Inventor: Renan Uflacker, 1075 Meader La., Mount Pleasant, S.C. 29565

[21] Appl. No.: 504,396

[22] Filed: Jul. 19, 1995

[51] Int. Cl.⁶ ........................................................ A61F 2/06
[52] U.S. Cl. ................... 623/1; 623/12; 606/194; 606/195
[58] Field of Search .................... 623/1, 12, 11; 606/194, 195

[56] References Cited

U.S. PATENT DOCUMENTS

| | | | |
|---|---|---|---|
| 3,657,744 | 4/1972 | Ersek | 3/1 |
| 3,894,530 | 7/1975 | Dardik | 623/1 |
| 4,140,126 | 2/1979 | Choudhury | 128/325 |
| 4,585,000 | 4/1986 | Hershenson | 128/345 |
| 4,617,932 | 10/1986 | Kornberg | 128/334 |
| 4,787,899 | 11/1988 | Lazarus | 623/1 |
| 5,078,726 | 1/1992 | Kreamer | 606/194 |
| 5,104,399 | 4/1992 | Lazarus | 623/1 |
| 5,211,658 | 5/1993 | Clouse | 623/1 |
| 5,219,355 | 6/1993 | Parodi et al. | 606/191 |
| 5,275,622 | 1/1994 | Lazarus et al. | 623/1 |
| 5,360,443 | 11/1994 | Barone et al. | 623/1 |
| 5,366,473 | 11/1994 | Winston et al. | 606/198 |
| 5,387,235 | 2/1995 | Chuter | 623/1 |
| 5,397,345 | 3/1995 | Lazarus | 623/1 |
| 5,456,713 | 10/1995 | Chuter | 623/1 |
| 5,489,295 | 2/1996 | Piplani et al. | 623/1 |
| 5,527,355 | 6/1996 | Ahn | 623/1 |
| 5,554,183 | 9/1996 | Nazari | 623/1 |

FOREIGN PATENT DOCUMENTS

0 461 791  12/1991  European Pat. Off. .......... A61F 2/06

Primary Examiner—Michael J. Milano
Assistant Examiner—Tram Anh T. Nguyen
Attorney, Agent, or Firm—Fish & Neave; Nicola A. Pisano

[57] ABSTRACT

Graft apparatus, delivery devices and methods for use in stent-graft systems are provided for use in treating aneurysms occurring in hollow-body organs or vessels and for treating arterio-venous fistulas. The graft and graft delivery devices provide the clinician with complete control over the location of the graft at any time prior to implantation of the stents, even when the graft is completely deployed from its introducer catheter. The graft and graft delivery devices also permit retrieval of the graft should it be desired to substitute a graft of a different size or to abort the procedure.

18 Claims, 6 Drawing Sheets

ADJUSTABLE AND RETRIEVABLE GRAFT AND GRAFT DELIVERY SYSTEM FOR STENT-GRAFT SYSTEM

FIELD OF THE INVENTION

The present invention relates generally to non-invasive techniques for repairing aneurysms occurring in hollow-body biological organs or vessels, for example, the abdominal aorta, and for repairing arterio-venous fistulas. More particularly, the present invention relates to methods and apparatus for repairing aneurysms and fistulas that permit adjustment and/or retrieval of the graft even after a deployment of the graft component of a stent-graft system.

BACKGROUND OF THE INVENTION

In recent years a number of non-invasive techniques have been developed to repair aneurysms occurring in hollow-body biological organs or vessels, for example, the abdominal aorta, using stent-graft techniques. These techniques generally seek to "reline" a flow path through the organ, for example, by fixing a graft across the weakened tissue of the aneurysm. The graft is then held in place with one or more stents, which may be implanted, for example, using a balloon catheter. Such arrangements are described, for example, in Parodi U.S. Pat. No. 5,219,355, European Application No. 0 461 791, and Clouse U.S. Pat. No. 5,211,658.

A drawback common to such previously known methods and apparatus, especially those such as the Parodi and Clouse patents, is the inability to adjust or retrieve the graft once it has been deployed from an introducer catheter. Generally, deployment of the graft (or the stent in Clouse system) marks a point of no-return — if the graft is determined to be in an inappropriate position, or the graft size is inadequate, it is not possible to abort the procedure.

Thus, previously known methods and apparatus cannot, for example, adjust the placement of the graft relative to the portions of the organ or vessel proximal and distal to the aneurysm (i.e., the proximal neck and the distal cuff of the aneurysm) once the graft is deployed. Neither can such methods and apparatus correct for migration of the graft between its deployment and fixation of the graft to the organ or vessel walls via stents, etc. See, for example, the catalog of complications resulting from mispositioning and/or migration described in T. Chuter et al. in *Endoluminal Vascular Prostheses*, Little Brown & Co. (1995), Chapter 3 at page 50, which is incorporated herein by reference.

Another drawback of previously known stent-graft systems, for example, those systems having integrated grafts and stents, is the large diameter introducer catheters needed to deliver such systems. A typical previously known stent-graft system may include a central delivery shaft having a diameter of 1.5–1.75 mm, a deployment balloon having a thickness of 0.50–0.75 mm, an anchoring stent with a thickness of 0.30–0.6 mm, a synthetic graft with a thickness of 0.25–0.5 mm, and a delivery sheath having a thickness of 0.50–0.75 mm. The stacking of these thicknesses results in a combined thickness of 4–7 mm, which must be inserted through a vascular system generally having a diameter in a range of 5–7 mm.

Not surprisingly, the large-diameter introducer catheters needed for such previously known stent-graft systems, for example, 22–26 French, create problems in delivering such systems transluminally via the femoral arteries, and the thicker diameters also reduce the clinician's ability to maneuver the stent-graft system into position along a tortuous path. See, for example, Chapter 3 of the foregoing text at pp. 40–41, 44 and 48, incorporated herein by reference, which describes spasm and delivery problems associated with the use of large introducer catheters employed with previously known stent-graft systems.

In view of the foregoing, it would be desirable to provide graft apparatus, delivery devices and methods for use in a stent-graft system for repairing an aneurysm that enable the graft position to be adjusted after deployment of the graft from an introducer catheter.

It further would be desirable to provide graft apparatus, delivery devices and methods for use in a stent-graft system for repairing aneurysms that enable the use of much smaller diameter introducer catheters than used with previously known stent-graft systems, thereby reducing problems associated with the use of large diameter introducer catheters.

It also would be desirable to provide graft apparatus, delivery devices and methods for use in stent-graft systems for repairing aneurysms that enable the graft to be entirely retrieved after initial deployment, for example, to be exchanged for a graft of a different size.

SUMMARY OF THE INVENTION

In view of the foregoing, it is an object of this invention to provide graft apparatus, delivery devices and methods for use in a stent-graft system for repairing aneurysms and fistulas that enable the graft position to be adjusted after deployment of the graft from an introducer catheter.

It is a further object of the present invention to provide graft apparatus, delivery devices and methods for use in a stent-graft system for repairing aneurysms and fistulas that enable the use of much smaller diameter introducer catheters than used with previously known stent-graft systems, thereby reducing problems associated with the use of large diameter introducer catheters.

It is another object of this invention to provide graft apparatus, delivery devices and methods for use in stent-graft systems suitable for excluding aneurysms in hollow-body organs and vessels other than the aorta, for example, in gastro-intestinal, respiratory, reproductive organ and urethral applications and elsewhere where it is desirable to "reline" a hollow-body organ or vessel, and for use in treating arterio-venous fistulas.

It is yet another object of this invention to provide graft apparatus, delivery devices and methods for use in stent-graft systems for repairing aneurysms and fistulas that enable a graft to be entirely retrieved after initial deployment from an introducer catheter, for example, to be exchanged for a graft of a different size.

These and other objects of the invention are accomplished in accordance with the principles of the invention by providing graft apparatus, delivery devices and methods for use in stent-graft systems that provide the clinician with complete control over the location of the graft, even after the graft is completely deployed from an introducer catheter. Thus, if a graft is determined to be mispositioned, the clinician may adjust the graft, or if the size is thought to be inappropriate, the clinician may even completely withdraw the graft and substitute a graft of a different size.

In accordance with the invention, the graft and stent components of a stent-graft system are separately delivered transluminally to the site of an aneurysm using small diameter catheters (e.g., 12–16 French for the graft, about 9–10 French for the stent). The graft component is removably engaged with proximal and distal manipulation leads that permit the location of the graft to be freely manipulated by the clinician after deployment from an introducer catheter. These manipulation leads even enable the graft to be fully retracted into its associated introducer catheter after deployment. The stent component of the system is likewise delivered transluminally to the site of the aneurysm via a small diameter introducer catheter, and permits use of a wide range of conventional stent designs to permanently fix the graft in position.

The invention further includes alternative embodiments of graft delivery devices suitable for use with a graft constructed in accordance with the present invention. These delivery devices provide complete control of over positioning of the graft, and permit quick release of the graft once its permanent position is selected.

Further features of the invention, its nature and various advantages will be more apparent from the accompanying drawings and the following detailed description of the preferred embodiments.

DETAILED DESCRIPTION OF THE PREFERRED EMBODIMENTS

The present invention provides methods and apparatus for treatment of aneurysms occurring in hollow-body organs or vessels, and for the treatment of arterio-venous fistulas, that overcome certain limitations of previously known non-invasive methods. In particular, the apparatus and methods of the present invention enable a clinician to adjust the positioning of a graft component of a stent-graft system once deployed from its associated introducer catheter, and even enable the clinician to entirely retrieve the graft should it be decided that a graft of a different size is required.

Figure 1A:
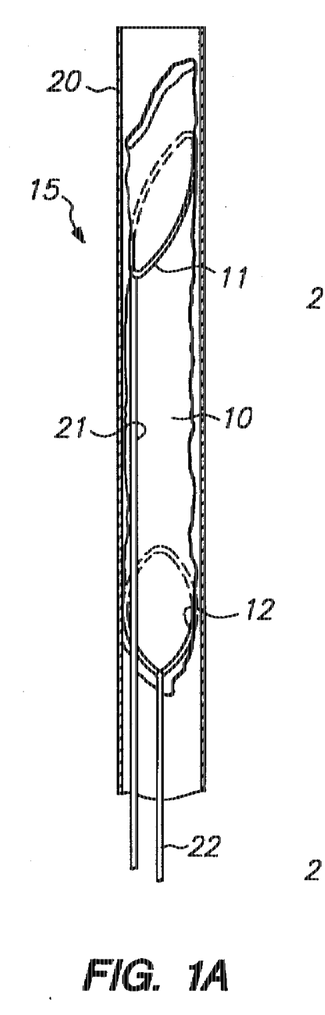
FIGS. 1A, 1B and 1C are, respectively, illustrative views of the deployment of a graft and delivery device constructed in accordance with the methods and apparatus of the present invention.
Figures 1B, 1C:
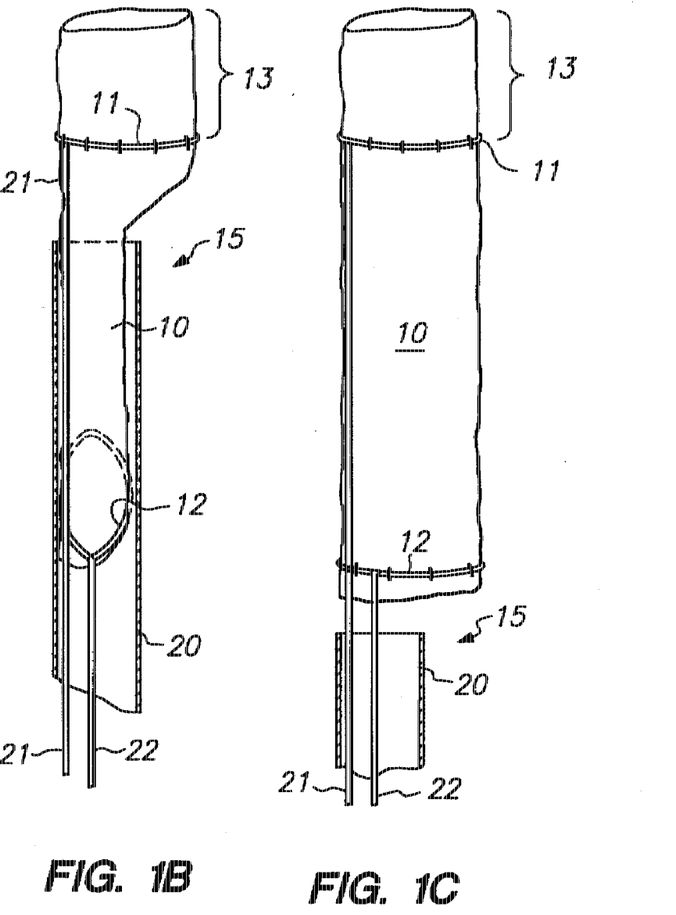

Referring to FIGS. 1A through 1C, graft 10 and the proximal end of delivery system 15 constructed in accordance with the principles of the present invention are described. Graft 10 is preferably a polyester fabric, such as DACRON®, a registered trademark of the E.I. duPont de Nemours Company, Wilmington, or other biocompatible material, such as PTFE (polytetrafluoroethylene) or tightly-woven wire mesh. One familiar to the art of non-invasive stent-graft technology will recognize that other suitable materials may be used in the construction of graft 10.

In accordance with the principles of the present invention, graft 10 includes two loops 11 and 12 located near its proximal and distal ends that are used for positioning the graft once it is deployed from its delivery device. Throughout this specification, proximal is used to refer, for example, in the context of the abdominal aorta, to the portion of the aorta nearer the renal arteries, while distal refers to the portion nearer to the iliac bifurcation. Loops 11 and 12 are formed of a flexible and sturdy material and are connected to graft 10, for example, by sutures, by incorporation into the wall of graft 10, by being weaved into the fabric of graft 10 or other suitable means.

In a first preferred embodiment, loops 11 and 12 comprise a nitinol (i.e., nickel-titanium) alloy wire. Alternatively, loops 11 and 12 may comprise a different metal alloy or a high strength plastic material. Loops 11 and 12 may be connected to the outer surface of graft 10, or alternatively may be connected to the interior surface of graft 10. In the latter case, the manipulation leads, described hereinafter, would be disposed within graft 10.

As will be understood from the description that follows, loops 11 and 12 must be made of a sufficiently resilient material to undergo significant elastic deformation, while retaining their ability to deploy graft 10. In addition, to assist in positioning graft 10 within the aneurysm or arterio-venous fistula under fluoroscopic guidance, loops 11 and 12 may be plated with a high contrast metal, for example, gold, platinum or tantalum.

Graft 10 is delivered transluminally to the site of an aneurysm in a hollow-body organ or vessel, for example, the abdominal aorta, while folded within delivery system 15 comprising introducer catheter 20 and manipulation leads 21 and 22, described in greater detail hereinafter. Introducer catheter 20 is shown in outline only in FIGS. 1 so as to not obscure salient aspects of the invention. Introducer catheter 20 may be of conventional construction and, in accordance with the present invention, is of a size between 12 and 16 French. Manipulation leads 21 and 22 are preferably constructed of a durable yet sturdy material, such as a nickel-titanium alloy.

As shown in FIGS. 1A to 1C, loop 11 is releasably engaged to manipulation lead 21, while loop 12 is likewise releasably engaged to manipulation lead 22. When folded within introducer catheter 20, loops 11 and 12 are elastically deformed to fit within the catheter. As seen in FIG. 1B, when introducer catheter 20 is withdrawn in a distal direction, the proximal end of graft 10 and loop 11 are deployed from the catheter, causing loop 11 to resume an approximately circular shape. As loop 11 recovers its original shape, graft 10 is opened from its folded shape.

Referring now to FIG. 1C, when introducer catheter 20 is withdrawn further in the distal direction, loop 12 and the distal portion of graft 10 are also deployed. When loop 12 opens upon deployment, graft 10 is preferably completely unfolded. Whereas with previously known graft members, complete deployment of the graft (as in FIG. 1C) would terminate the clinician's ability to adjust or retrieve the graft member, in accordance with the present invention, graft 10 remains coupled to manipulation leads 21 and 22.

Thus, even though graft 10 is deployed, its position may be adjusted within the aneurysm, by pulling (or pushing) one or both of manipulation leads 21 and 22 in the proximal or distal directions. In addition, should the clinician determine that graft 10 is of inappropriate size, or should he for some other reason wish to abort the procedure, graft 10 may be completely recovered within introducer catheter 20 by advancing catheter 20 in the proximal direction while retaining manipulation leads 21 and 22 against proximal movement. Graft 10 will accordingly be retracted within introducer catheter 20 as the catheter advances in the proximal direction.

In the illustrative embodiment of FIGS. 1, loop 12 connected to the distal end of graft 10 is preferably located at or near the lower end of the graft to facilitate retraction of graft 10 within introducer catheter 20. By positioning loop 12 in this manner, it is expected that the possibility of inadvertently catching graft 10 on introducer catheter 20 will be reduced, ensuring complete retrievability of the graft even if fully deployed.

On the other hand, in the embodiment of FIGS. 1, loop 11 is preferably connected to the graft at a distance below the proximal edge of graft 10, thus creating an overhang region 13 (see FIGS. 1B and 1C) of approximately 15-20 mm. Overhang region may have a length of about two-thirds of the length of the stent to be used in fixing graft 10 in place within the aorta. This positioning of loop 11 on graft 10 is expected to prevent interference between loop 11 and the stent to be implanted.

Alternatively, as described with respect to FIGS. 2, it may instead be desirable to omit overhang region 13 so that loop 11 is located at or near the proximal (upper) end of graft 10, so as to prevent potential flutter of the overhang when introduced into high flow rate environments. In this case loop 11 is captured and expanded by the proximal stent when it is deployed, and loop 11 includes elongated leads that traverse the length of the overhang and permit the engagement means to engage loop 11 at a point distal to overhang region 13.

Turning now to FIGS. 2A, 2B, 2C and 2D, several alternative embodiments are described for releasably engaging loops 11 and 12 of graft 10 to manipulation leads 21 and 22, respectively. For clarity, only loop 11 is discussed here, although loop 12 may include a similar engagement arrangement.

Figure 2A:
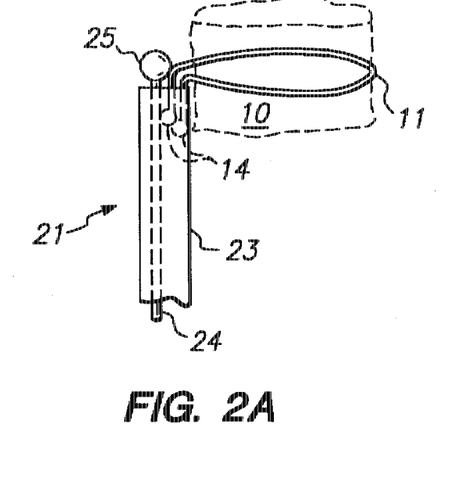
FIGS. 2A, 2B, 2C and 2D are, respectively, alternative embodiments for engaging the graft of FIGS. 1 to the manipulation leads of a delivery device constructed in accordance with the present invention.
Figure 3:
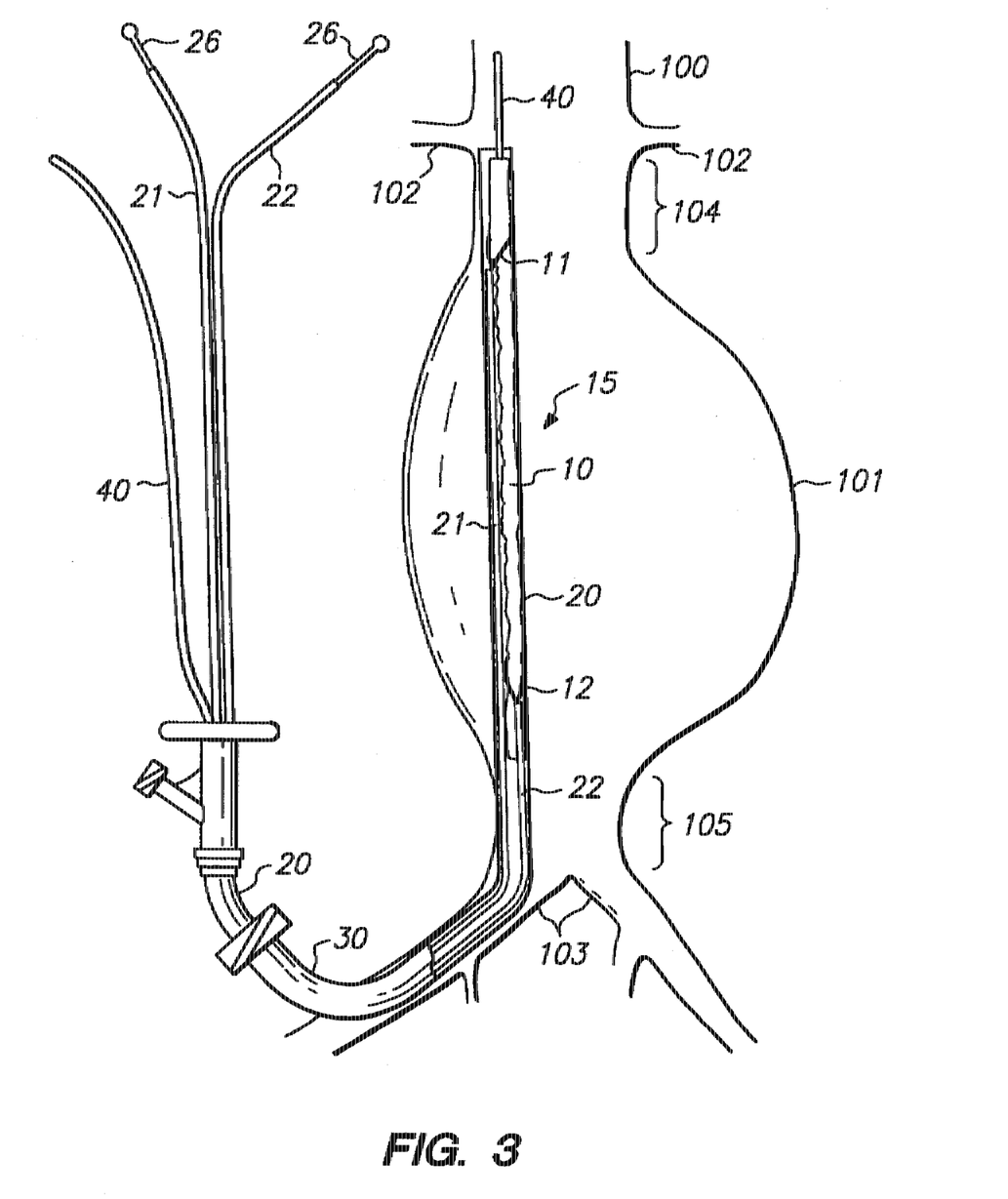
FIG. 3 is an elevational view, partly in section, showing positioning of the graft of FIG. 1 being positioned in an abdominal aortic aneurysm.

In FIG. 2A, loop 11 terminates in beads 14 disposed on its ends. Manipulation lead 21 includes outer sheath 23, push wire 24 and ball 25. As will of course be understood, the distal end of manipulation lead 21 extends outside of the patients' body via an introducer sheath. As seen in FIG. 3, the distal ends of manipulation leads 21 and 22 each include mechanism 26, for example, a spring-loaded shaft, for releasing the grip of manipulation leads 21 and 22 on loops 11 and 12, respectively.

Push wire 24 is biased in a distal direction, so that when beads 14 of loop 11 are inserted within the proximal end of outer sheath 23, ball 25 captures the beads within the outer sheath, thus releasably engaging loop 11 to manipulation lead 21. When mechanism 26 is later actuated, for example, by pushing push wire 24 in a proximal direction, ball 25 is lifted away from the proximal end of outer sheath 23, and beads 14 and loop 11 are set free.

Accordingly, manipulation lead 21 can be pulled in the proximal and distal directions to adjust the positioning of proximal end of graft 10 via its engagement with loop 11. Once the graft is in a desired position within the neck of the aneurysm, mechanism 26 is actuated to release loop 11. Loop 11 is retained on the outer surface of graft 10. Because beads 14 may be separately formed on the ends of loop 11, loop 11 may be opened to an even larger diameter when a stent is expanded into position within graft 10.

Figure 2B:
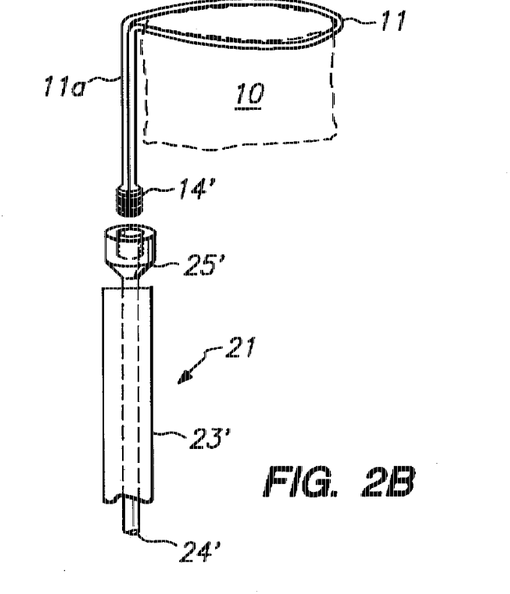

Referring now to FIG. 2B, an alternative embodiment of the engagement means for coupling loop 11 to manipulation lead 21 is described. As seen in FIG. 2B, loop 11 is designed for placement at the proximal end of graft 10, thereby omitting overhang region 13. Instead, loop 11 includes elongated leads 11a that extend distally for approximately the same length as the now omitted overhang region 13, for example 15-20 mm, depending upon the type of stent to be used. Loop 11 therefore keep the proximal end of graft 10 patent even in high flow environments, while elongated leads 11a permit loop 11 to remain engaged with manipulation lead 21 until after the proximal stent is fixed into position.

In the embodiment of FIG. 2B, the ends of elongated leads 11a terminate in threaded region 14'. Manipulation device 21 includes outer sheath 23', wire 24' and threaded socket 25'. The distal end of manipulation lead 21 terminates in mechanism 26' that enables wire 24' to be rotated within outer sheath 23'. During deployment of graft 10, threaded portion 14' of loop 11 is threadedly engaged with threaded socket 25'. Once graft 10 is in its desired position, the proximal stent is deployed. The clinician then operates mechanism 26' to rotate wire 24', thus unscrewing threaded portion 14' of loop 11 from threaded socket 25'. Because elongated leads 11a extend distally beyond the distal end of the proximal stent, manipulation lead 21 may be uncoupled from loop 11 without interfering with the deployed proximal stent.

Figure 2C:
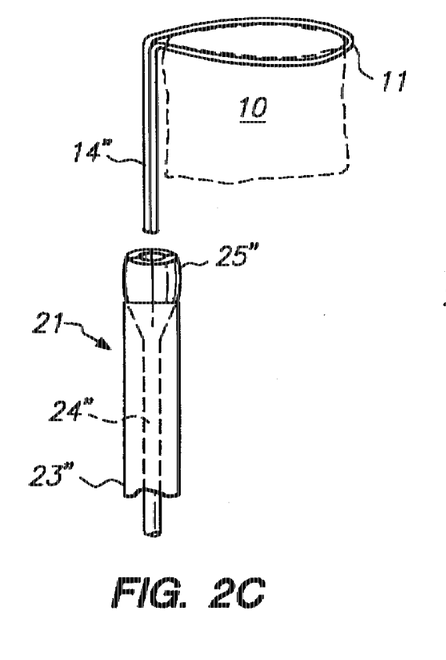

With respect to FIG. 2C, another alternative embodiment of an engagement means suitable for use with graft 10 of the present invention is described. In this embodiment, again suitable for use without overhang region 13, loop 11 terminates with elongated right-angled lengths 14". Manipulation lead 21 includes outer sheath 23", push wire 24" and collet 25". The distal end of manipulation lead 21 terminates in mechanism 26", for example a spring-loaded shaft.

Collet 25" is illustratively formed of four opposing members, while push wire 24" is biased in a distal direction. This biasing of push wire 24" causes the outer surfaces of the opposing members of collet 25" to be urged against the inner surface of outer sheath 23', thereby urging the opposing members comprising collet 25" into contact with one another.

To insert right-angled ends 14" of loop 11 into collet 25", push wire 24" is first urged in a proximal direction, relieving the contact forces between the opposing members of collet 25" to permit right-angled ends 14" to be inserted therebetween. Push wire is then permitted to return to its biased position, thereby capturing right-angled ends 14" within collet 25" and thus releasably engaging loop 11 to manipulation lead 21. When mechanism 26" is subsequently actuated (after deployment of graft 10), for example, by urging push wire 24" in a proximal direction, the opposing members of collet 25" relax their grip on right-angled ends 14" of loop 11, thus setting loop 11 free.

Figure 2D:
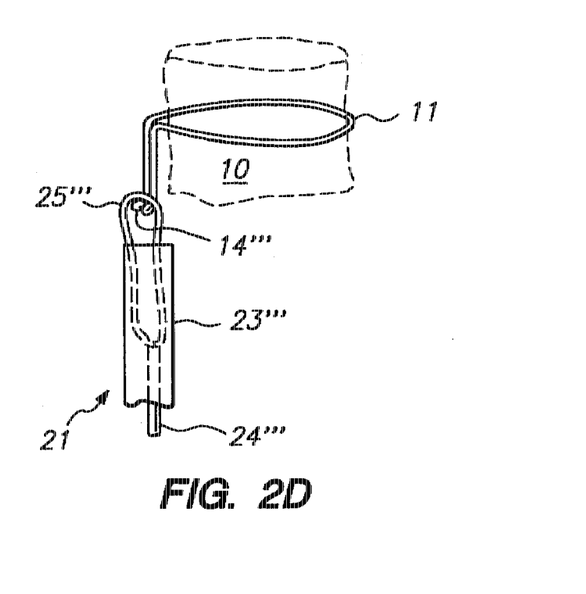

Referring now to FIG. 2D, a yet further alternative embodiment of an engagement means suitable for use with the present invention is described. In FIG. 2D, loop 11 terminates in beads 14''' that are captured in snare 25''' connected to the proximal end of push wire 24'''. Manipulation lead 21 includes an actuation mechanism 26''' at its distal end that biases snare 25''' in a distal direction, thereby engaging beads 14''' within snare 25'''. Manipulation lead 21, including outer sheath 23''', snare 25''', beads 14''' and loop 11 are therefore movable as a unit in the proximal and distal directions, while actuation of mechanism 26''' causes snare 25''' to release beads 14'''.

The foregoing means of coupling loops 11 and 12 to manipulation leads are intended to be merely illustrative, and other suitable engagement arrangements may occur to those of skill in the art of stent-graft design. Thus, for example, any of the above-described engagement means could be used with a graft having overhang region 13, or loop 11 could instead have elongated leads 11a, thereby enabling omission of overhang region 13.

Moreover, graft 10 also may have integrated within it elastic fibers that assist the graft in opening once it is deployed. For such a graft, it would no longer be necessary for loops 11 and 12 to assist in opening the graft, and loops 11 and 12 may then consist of, for example, a flexible thread or wire. In this case, the flexible thread or wire could be removed completely from graft 10, for example, by cutting the wire at the distal end and pulling the entire length of wire out through the introducer sheath.

Figure 4:
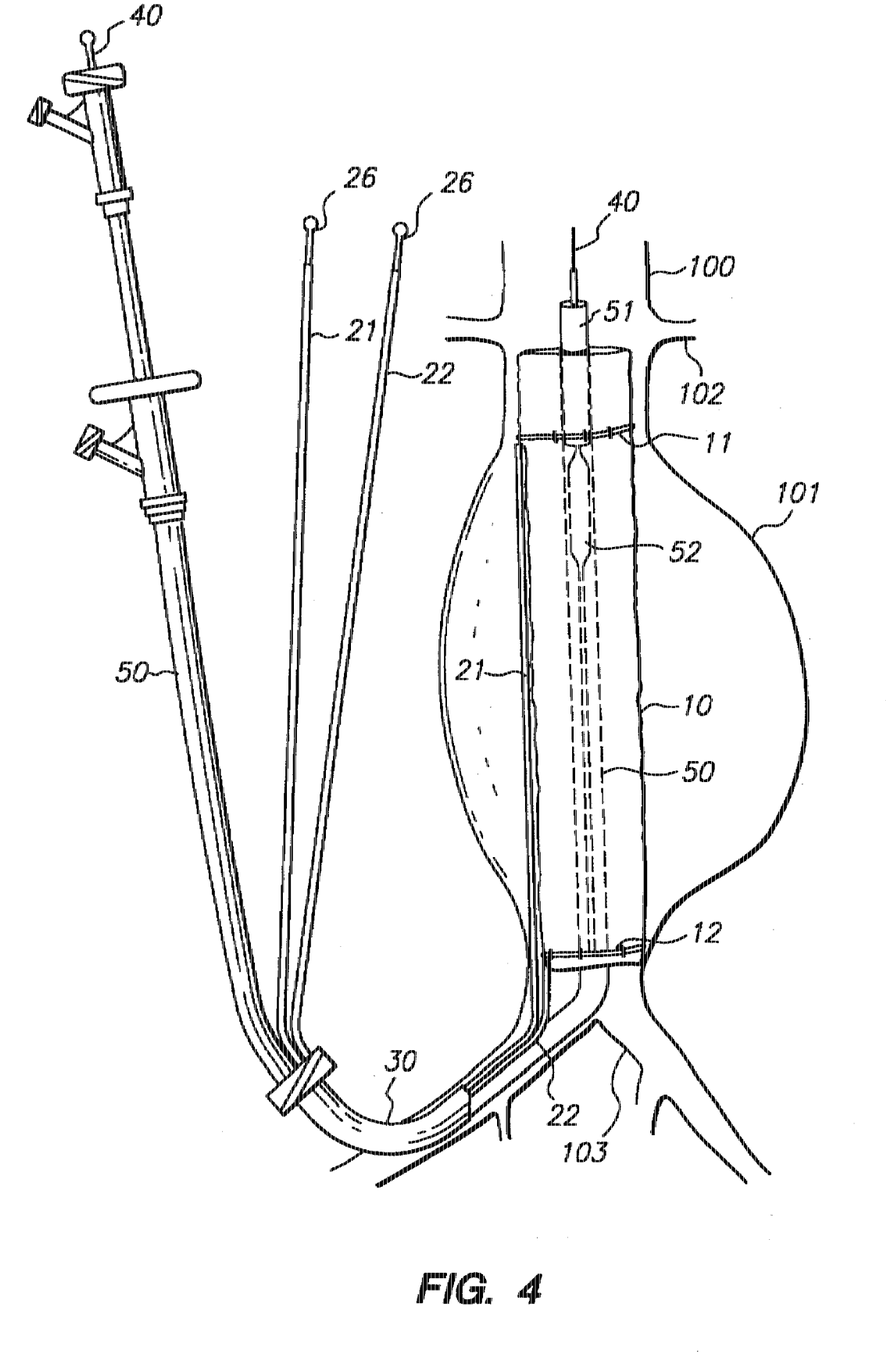
FIG. 4 is an elevational view, partly in section, showing deployment of the graft of FIG. 3.
Figure 5:
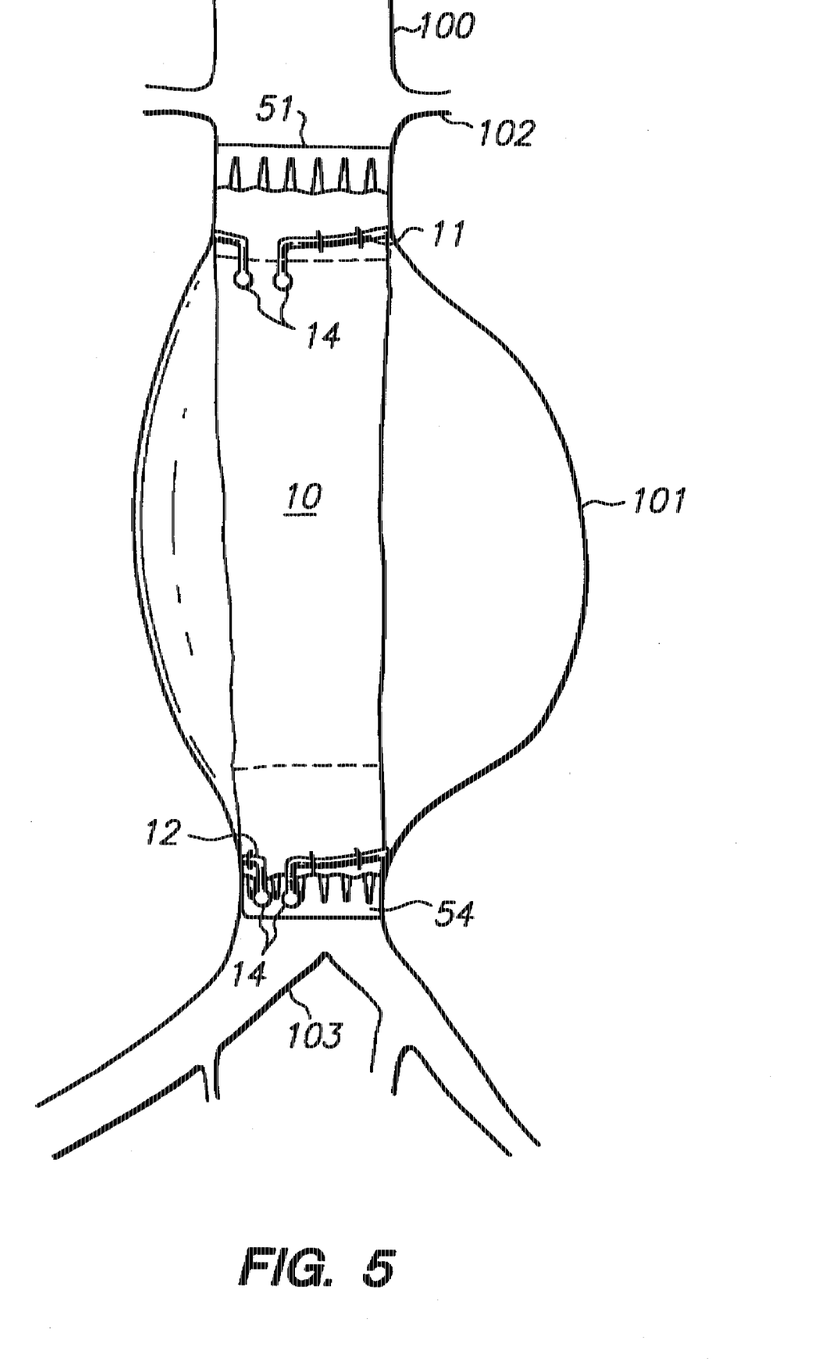
FIG. 5 is an elevational view of a graft constructed in accordance with the present invention, as permanently implanted in the aorta.

Referring now to FIGS. 3–5, a method of implanting a graft constructed in accordance with the present invention within an abdominal aorta aneurysm is described. As illustratively shown in FIG. 3, graft 10 of the stent-graft system is disposed across the region of aneurysm 101 in aorta 100, which is located between renal arteries 102 and iliac arteries 103. Aneurysm 101 includes a proximal nondilated region of aorta 100 above the aneurysm referred to as "proximal neck" 104, and a distal region just above the bifurcation for iliac arteries 103 referred to as "distal cuff" 105.

Graft 10 includes proximal and distal loops 11 and 12 connected to manipulation leads 21 and 22, as described hereinabove. Graft 10 is threaded through a femoral artery in introducer catheter 20 via introducer sheath 30 along guidewire 40, so that graft 10 is positioned across aneurysm 101. In accordance with the present invention, graft 10 permits introducer catheter 20 to have a smaller diameter, for example 12–16 French, relative to previously known apparatus that generally use diameters greater than 21 French. The position of introducer catheter 20 within aneurysm 101 may be determined using standard fluoroscopic techniques and a suitable high contrast agent on introducer catheter 20 or graft 10.

In FIG. 4, graft 10 is shown fully deployed from introducer catheter 20 (which has been removed). Manipulation leads 21 and 22 are used to maneuver graft 10 to a desired location across aneurysm 101, by moving manipulation leads 21 and 22 in the proximal and distal directions under fluoroscopic guidance. When graft 10 has been moved to a desired position, catheter 50 containing collapsed stent 51 and deployment balloon 52 is inserted along guidewire 40 so that the stent is positioned overlapping the proximal end of graft 10. As described hereinabove with respect to FIGS. 1A through 1C, the position of graft 10 may be adjusted, or the graft entirely withdrawn, at any point up to implantation of proximal stent 51.

Stent 51 suitable for use with graft 10 of the present invention may be of any design that will cause fixation of graft 10 to the walls of aorta 100. For example, stent 51 may comprise an elastically balloon-expanded rolled sheet, as described, for example in Kreamer U.S. Pat. No. Re. 34,327, a plastically balloon-deformable wire mesh, as described for example, in Palmaz U.S. Pat. No. 4,733,665 and Gianturco U.S. Pat. No. 5,314,444, a thermally activated stent as described in Dotter U.S. Pat. No. 4,503,569, or an elastically self-expanding stent as described in McNamara U.S. Pat. No. 5,147,370, the disclosures of which are incorporated herein by reference. Stents suitable for use with the graft system of the present invention preferably employ a delivery catheter having a diameter of about 9–10 French.

Referring to FIG. 5, graft 10 of FIG. 4 is shown affixed to the walls of aorta 100 by stents 51 and 54. Stents 51 and 54 may be positioned and expanded into apposition with graft 10 and the walls of aorta 100 through introducer catheter 20 as described above with respect to FIG. 4. Alternatively, the delivery catheter and stents 51 and 54 may be delivered to the respective ends of graft 10 via the femoral artery associated with the right branch of the iliac artery, or even from above via the brachial/carotid artery.

During placement of stents 51 and 54, manipulation leads 21 and 22 of the graft system are held in position, for example, under fluoroscopic guidance, to prevent flow-induced migration of graft 10. Either immediately before, or during, the expansion of stent 51, mechanism 26 of manipulation lead 21 is actuated to release loop 11, and the manipulation lead is then withdrawn.

As will of course be apparent, releasing ends 14 of loop 11 as stent 51 expands to fix graft 10 in position permits the loop to increase in diameter to accommodate the expanding stent. Thus, as seen in FIG. 5, a gap may develop between ends 14 of loop 11 as it is captured between the walls of aorta 100 and graft 10 by the expanding stent. Stent 54 is expanded in a manner similar to that for stent 51, with manipulation lead 22 releasing loop 12 either before or during expansion of stent 54.

Alternatively, if a sufficiently long overhang 13 is provided for graft 10, or if elongated leads 11a are instead provided on graft 10 and loop 11 is connected at or near the proximal end of graft 10, stent 51 may be expanded into position prior to releasing loop 11 from manipulation lead 21. Manipulation lead is then uncoupled from loop 11 once the proximal stent has been deployed.

Figure 6A:
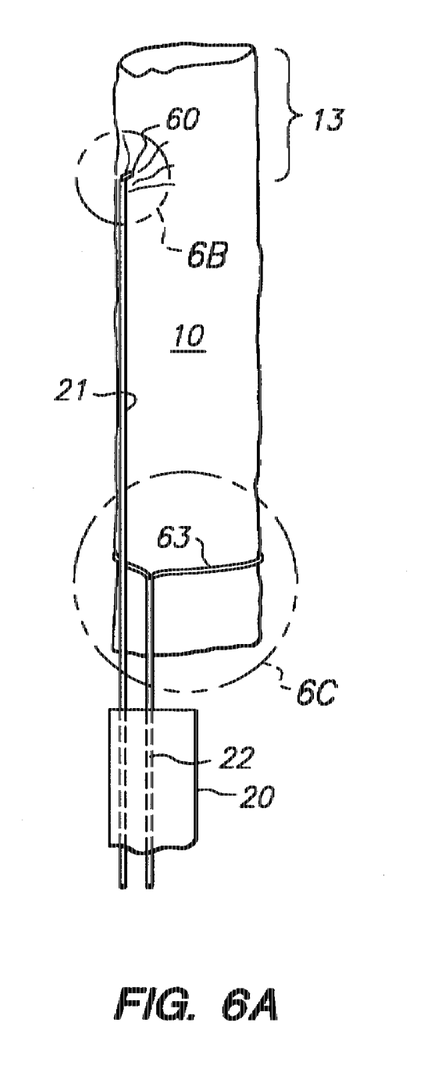
FIGS. 6A, 6B and 6C are, respectively, an elevational view and detail views of an alternative embodiment of the graft and delivery device of the present invention.
Figure 6B:
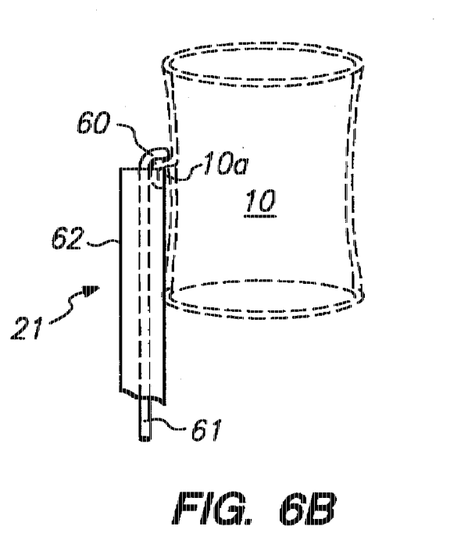
Figure 6C:
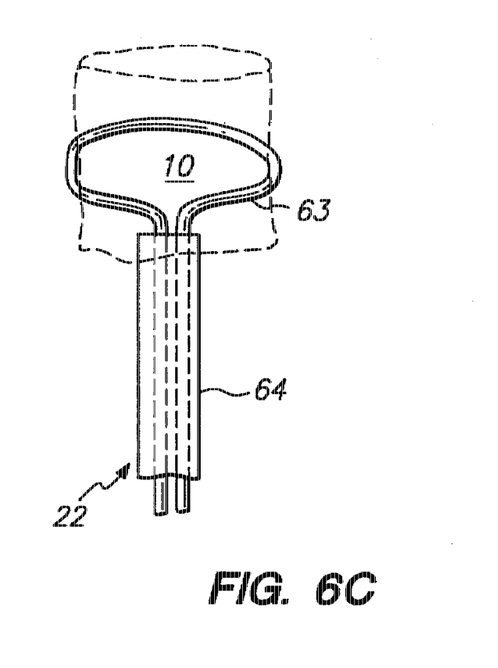

Referring now to FIGS. 6A to 6C, a yet further alternative embodiment of the graft and delivery system of the present invention is described. In FIG. 6A, graft 10 is shown fully deployed from introducer catheter and engaged with manipulation leads 21 and 22. As shown in detail in FIG. 6B, fold 10a of graft 10 is pinched between hook 60 of wire 61 and outer sheath 62 of manipulation lead 21. As for the engagement means of FIGS. 2, the hook 60 is connected via wire 61 to an actuation mechanism at the distal end of manipulation lead 21. Wire 61 and hook 60 may be spring-biased in the distal direction to graspingly engage graft 10 near its proximal end.

With respect to FIG. 6C, the distal portion of graft 10 is manipulated using snare 63 that grasps the distal portion of the graft. Snare 63 is disposed within outer sheath 64, and is operable via a suitable mechanism located at the distal end of manipulation lead 22. Snare 63 is not connected to graft 10 other than by operation of snare 63, so that when snare 63 is expanded, snare 63 may slide off of graft 10.

Implantation of the graft of FIGS. 6 is accomplished in a manner similar to that described above with respect to FIGS. 3–5. First, the introducer catheter is delivered transluminally to the site of the aneurysm. The introducer catheter is then retracted while manipulation leads 21 and 22 are held in position, so that graft 10 is deployed as shown in FIG. 6A. Manipulation leads 21 and 22 may be moved in the proximal or distal directions to adjust the location of graft 10, or may even be fully retracted within the introducer catheter to retrieve the graft. As will of course be understood, introducer catheter is transported along a suitable guidewire, so that the guidewire is disposed with graft 10 once it is deployed from the introducer catheter.

With the introducer catheter fully removed, a stent delivery catheter is transported either along the guidewire already disposed through graft 10, or a separate guidewire delivered via the same or a different access artery. A proximal stent is then deployed to engage the proximal neck of the aneurysm and the proximal end of graft 10 (in overhang region 13). Manipulation lead 21 is then actuated so that hook 60 releases its grasp on graft 10, and manipulation lead 21 and the stent delivery catheter are withdrawn.

With the proximal stent fixing the proximal end of graft 10 in place, snare 63 is opened and manipulation lead 22 retracted in the distal direction. These operations permit snare 63 to slide off the distal end of graft 10, while the guidewire remains disposed through the interior of graft 10. A distal stent delivery device is then transported along the same or a different guidewire into position at the distal end of graft 10, and a distal stent is deployed.

The result of the above implantation method appears similar to FIG. 5, except that in accordance with the embodiment of FIGS. 6, no loops 11 and 12 are used or left connected to the graft once it is implanted. As will be appreciated, however, the graft, delivery device and methods described hereinabove with respect to the embodiment of FIGS. 6 permit the graft to be fully adjustable and retrievable up until the proximal stent is deployed.

It will of course be understood by those skilled in the relevant arts that the exemplary embodiments of the invention described hereinabove in no way limit the intended use of the methods and apparatus of the present invention, and that the methods of the present invention could be implemented using graft delivery devices having other configurations.

In addition, while the methods and apparatus of the present invention have been described with reference to excluding aneurysms occurring in the abdominal aorta, the methods and apparatus of the present invention are equally applicable to gastro-intestinal, respiratory, reproductive organ and urethral applications and elsewhere where is desirable to "reline" a hollow-body organ or vessel, and for repairing arterio-venous fistulas.

While preferred illustrative embodiments of the present invention are described above, it will be obvious to one skilled in the art that various changes and modifications may be made therein without departing from the invention and it is intended in the appended claims to cover all such changes and modification which fall within the true spirit and scope of the invention.

What is claimed is:

1. Apparatus for transluminally delivering a graft to treat an aneurysm, the apparatus comprising:

a graft having first and second end regions, a loop affixed to the graft near the first end region, the loop including first and second ends and a predetermined circumference, the loop assuming an elongated shape when compressed for delivery and resuming an expanded shape when the graft is deployed, the loop spreading the graft to an expanded diameter, when the graft is deployed, substantially without the loop sliding relative to the graft;

a delivery device including an introducer catheter having a bore for accepting the graft and a manipulation lead, the manipulation lead having a first end disposed within the bore; and means for releasably engaging each of the first and second ends of the loop to the manipulation lead, the manipulation lead permitting adjustment of the position of the graft after the graft is deployed from the bore of the introducer catheter.

2. The apparatus as defined in claim 1 wherein the introducer catheter has a diameter less than 16 French.

3. The apparatus as defined in claim 1 wherein the means for releasably engaging the first and second ends of the loop comprises:

beads formed on the first and second ends of the loop;

a portion of the first end of the manipulation lead defining a cavity for receiving the beads, a push wire mounted for reciprocation through the cavity, and a ball mounted on an end of the push wire to retain the beads in the cavity; and an actuation mechanism disposed on a second end of the manipulation lead for causing reciprocation of the push wire, so that when the actuation mechanism is actuated the beads are releasably engaged within the cavity by the ball.

4. The apparatus as defined in claim 3, further comprising:

a hook mounted on a first end of a second manipulation lead; and an actuation mechanism disposed on a second end of the second manipulation lead and coupled to the hook for causing the hook to selectively grasp and release the graft.

5. The apparatus as defined in claim 1 wherein the means for releasably engaging the first and second ends of the loop comprises:

a threaded portion formed from the first and second ends of the loop;

a portion of the first end of the manipulation lead defining a threaded socket that receives the threaded portion; and an actuation mechanism disposed on a second end of the manipulation lead for causing rotation of the threaded socket, so that rotation of the manipulation lead in a first direction causes engagement of the threaded portion to the threaded socket, and rotation of the manipulation lead in a second direction causes disengagement of the threaded portion and the threaded socket.

6. The apparatus as defined in claim 5 further comprising:

a hook mounted on a first end of a second manipulation lead; and an actuation mechanism disposed on a second end of the second manipulation lead and coupled to the hook for causing the hook to selectively grasp and release the graft.

7. The apparatus as defined in claim 1 wherein the means for releasably engaging the first and second ends of the loop comprises:

a collet mounted on the first end of the manipulation lead to engage the first and second ends of the loop; and an actuation mechanism disposed on a second end of the manipulation lead and coupled to the collet, so that when the actuation mechanism is actuated the first and second ends of the loop are releasably engaged within the collet.

8. The apparatus as defined in claim 7 further comprising:

a hook mounted on a first end of a second manipulation lead; and an actuation mechanism disposed on a second end of the second manipulation lead and coupled to the hook for causing the hook to selectively grasp and release the graft.

9. The apparatus as defined in claim 1 wherein the means for releasably engaging the first and second ends of the loop comprises:

beads formed on the first and second ends of the loop;

a portion of the first end of the manipulation lead defining a bore, a wire mounted for reciprocation through the bore, and a snare mounted on an end of the wire to engage the heads; and an actuation mechanism disposed on a second end of the manipulation lead for causing reciprocation of the wire, so that when the actuation mechanism is actuated the beads are released from engagement with the snare.

10. The apparatus as defined in claim 9 further comprising:

a hook mounted on a first end of a second manipulation lead; and an actuation mechanism disposed on a second end of the second manipulation lead and coupled to the hook for causing the hook to selectively grasp and release the graft.

11. The apparatus as defined in claim 1 wherein the manipulation lead includes a bore and the means for releasably engaging the first and second ends of the loop comprises:

portions of the first and second ends of the loop which extend through the bore.

12. The apparatus as defined in claim 1 further comprising:

a hook mounted on a first end of second manipulation lead; and an actuation mechanism disposed on a second end of the second manipulation lead and coupled to the hook for causing the hook to selectively grasp and release the graft.

13. A graft for transluminally delivering a graft to treat an aneurysm, the apparatus comprising:

a graft having a first end region and a first loop affixed near the first end region, the first loop having free ends an a predetermined circumference, the first loop assuming an elongated shade when compressed for delivery and resuming an expanded shape when the graft is deployed, the first loop the graft to an expanded diameter, when the graft is deployed, substantially without the first loop sliding relative to the graft;

a delivery device including an introducer catheter having a bore for accepting the graft, first and second manipulation leads each having a first end disposed within the bore, and engagement means for releasably engaging each of the free ends of the first loop, the engagement means connected to the first end of each one of the first and second manipulation leads, respectively.

14. The apparatus as defined in claim 13, wherein the introducer catheter has a diameter less than 16 French.

15. The apparatus as defined in claim 13 wherein the graft includes a second loop including free ends and wherein the engagement means comprises:

beads formed on the free ends of the first and second loops;

means for releasably engaging the beads connected to the first end of each one of the first and second manipulation leads; and an actuation mechanism disposed on a second end of each one of the first and second manipulation leads.

16. The apparatus as defined in claim 13 wherein the graft includes a second loop including free ends and wherein the engagement means comprises:

a threaded portion formed on the free ends of each one of the first and second loops;

a portion of the first end of each one of the first and second manipulation leads defining a threaded socket that receives the threaded portion; and an actuation mechanism disposed on a second end of each one of the first a d second manipulation leads for causing rotation of the threaded socket.

17. The apparatus as defined in claim 13 wherein the graft includes a second loop, including free ends and wherein the engagement means comprises:

a collet mounted on the first end of each one of the first and second manipulation leads to engage the free ends; and an actuation mechanism disposed on a second end of each one of the first and second manipulation leads and coupled to a respective collet.

18. The apparatus as defined in claim 13 wherein the engagement means comprises:

means disposed from the first manipulation lead for grasping a portion of the graft;

a snare disposed from the second manipulation lead for snaring the free ends of the first loop; and an actuation mechanism disposed on a second end of each one of the first and second manipulation leads and coupled to the means for grasping the snare, respectively.

\* \* \* \* \*